United States Patent [19]

Chang et al.

[11] Patent Number: 5,041,726
[45] Date of Patent: Aug. 20, 1991

[54] INFRARED HOLOGRAPHIC DEFECT DETECTOR

[75] Inventors: David B. Chang, Tustin; James E. Drummond, Oceanside, both of Calif.

[73] Assignee: Hughes Aircraft Company, Los Angeles, Calif.

[21] Appl. No.: 535,793

[22] Filed: Jun. 11, 1990

[51] Int. Cl.⁵ ............................................. G01B 9/021
[52] U.S. Cl. ................................. 250/341; 250/358.1; 356/347; 356/359; 356/237
[58] Field of Search ............................. 250/341, 358.1; 356/359, 360, 347, 237; 350/3.6

[56] References Cited

U.S. PATENT DOCUMENTS

| | | | |
|---|---|---|---|
| 4,506,981 | 3/1985 | Hoff, Jr. | 356/347 |
| 4,645,291 | 2/1987 | McCrickerd | 350/3.83 |
| 4,647,196 | 3/1987 | Kuni et al. | 356/237 |
| 4,752,140 | 6/1988 | Cielo et al. | 356/358 |
| 4,869,593 | 9/1989 | Biegen | 356/359 |

*Primary Examiner*—Carolyn E. Fields
*Assistant Examiner*—Drew A. Dunn
*Attorney, Agent, or Firm*—Michael W. Sales; Wanda Denson-Low

[57] ABSTRACT

An infrared holographic defect detector (10) comprises a far infrared pulsed coherent source (14) of infrared radiation which provides infrared radiation. The radiation is directed at a generally non-reflective surface (12), for example, a surface of an automobile body having a matt grey pre-coat thereon. A semi-transparent mirror (15) is placed in the path of the radiation to provide a reference beam (17) therefrom. An infrared detector (18) and a charge-coupled device (20) receives the radiation reflected from the surface and the reference signal. A comparator (22) compares the received reflected information and the reference signal and, preferably, information from a source (24) which defines a desired surface configuration in order to derive a quantitative measurement of the surface. A monitor (26) visually displays the quantitative mesurement and location of any dents in the surface. To avoid a requirement that sequential automobile doors containing the surface of investigation be three-dimensionally aligned to within microns of reference points, a detector of the reflected radiation can be translated and rotated. A number of sensed images of the surface are taken, one at each of the different positions of the detector. For each image a measure of its correlation with the standard image is made.

11 Claims, 1 Drawing Sheet

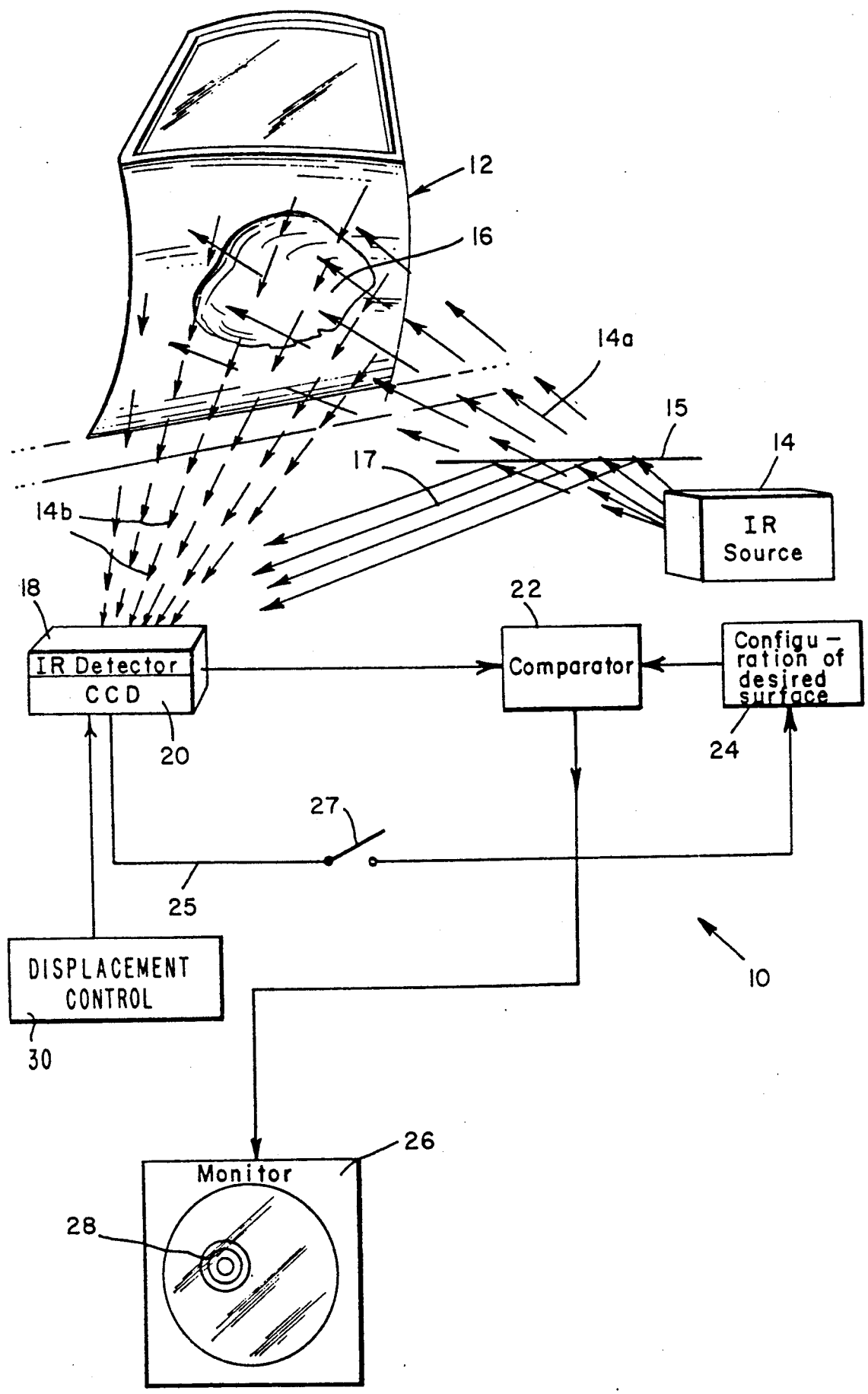

INFRARED HOLOGRAPHIC DEFECT DETECTOR

BACKGROUND OF THE INVENTION

The present invention relates to a method and apparatus for detecting and measuring irregularities in surfaces, in particular, by using holographic interference techniques for evaluating such irregularities.

Visual inspection of surfaces becomes difficult in the presence of inadequate light and even more so when the surfaces are not reflective. For example, the exterior surfaces of automobile bodies are covered with several coats of paint, including a matt grey pre-coat and a final specularly reflecting coat. If the surface is dented or has any other imperfection therein, the dent is far less easily detectable by visual inspection in the matt grey pre-coat than in the final specularly reflecting coat. Therefore, if the dent in the surface is not within tolerance, and is not seen until after application of the final specularly reflecting coat, it becomes more expensive in time, labor and materials to repair the finally coated surface than one which has not been so coated.

SUMMARY OF THE INVENTION

These and other considerations are successfully addressed in the present invention by obtaining information of interference patterns derived from infrared radiation reflected from a surface under investigation and from reference radiation. Preferably, the interference pattern information is compared with information of a standard, such as a desired surface configuration, in order to determine how greatly the actual surface varies from the standard and to determine if the surface under test passes or fails, and to the extent of passing or failure, and the location of any defects. If needed, the surface is reprocessed.

To avoid a requirement that sequential parts, such as automobile doors, containing the surface of investigation be three-dimensionally aligned to within microns of reference points, a detector of the reflected radiation can be translated and rotated. A number of sensed images of the surface are taken, one at each of the different positions of the detector. For each image a measure of its correlation with the standard image is made.

Several advantages are derived from this arrangement. Inspection of surface quality is determined as soon as practicable, before further work is performed, such as application of the final or even a preliminary coating, thus avoiding the need and expense of reworking defects detected later in the production process by conventional visual defect detection methods which require a specularly reflecting surface. The degree of possible imperfections is also obtainable and measured under pass/fail conditions. Costs in processing are reduced through savings in time, labor and material. Large areas can be rapidly scanned by high-lighting irregularities and by providing information as to their depths and locations.

Other aims and advantages, as well as a more complete understanding of the present invention, will appear from the following explanation of an exemplary embodiment and the accompanying drawing thereof.

DESCRIPTION OF THE DRAWING

The sole FIGURE illustrates a realization of the present invention, embodied for detecting irregularities in the door of an automobile.

DETAILED DESCRIPTION OF THE PREFERRED EMBODIMENT

As shown in the sole illustration, an infrared holographic defect detector 10 is used to determine the existence, location and extent of surface irregularities in a door 12 of an automobile. Detector 10 includes a source 14 of infrared (IR) energy or radiation 14a, which is directed at an area 16 on the door. A semitransparent mirror 15 is also positioned in the path of radiation 14a emanating from source 14 to provide a reference beam 17.

An IR detector array of rectifying elements 18, coupled to a charge-coupled device (CCD) 20, is placed adjacent to area 16, and is positioned in the paths of the IR radiation reflected as radiation 14b from area 16 and of reference beam 17, in order to obtain an interference pattern therefrom.

Charge-coupled device 20 converts the detected radiation into appropriate electric signals, which may be converted visually to directly display the interference pattern obtained from reflected radiation 14b and reference beam 17.

It is preferred, however, that more detailed information be obtained, specifically of a comparison between what is obtained from the configuration of an actual door area 16 and the configuration of a desired surface. Accordingly, the signals from charge-coupled device 20 are forwarded to a comparator 22. Information is also supplied to comparator 22 from a reference source 24, in which the configuration of the desired surface is defined in suitable electronic form, such as in terms of a holographic interference pattern.

This information of the desired surface configuration is obtained by use of a link 25 between charge-coupled device 20 and reference source 24. A switch 27 is positioned in link 25 for selective opening and closure. This information of the desired surface configuration is obtained from a model of a desired surface, which is first used in place of door 12 under test. Radiation 14a from source 14 is directed at the model surface for obtaining a reflection therefrom. The reflected radiation as well as that from reference beam 17 is detected by IR detector 18 and charge-coupled device 20. The signals therefrom are directed through link 25 and closed switch 27 to source 24 for storage therein. Thereafter, switch 27 is opened when detector 10 is to be used for inspecting door 12.

For such inspection, comparator 22 compares the information from reference beam 17 and reflected radiation 14b, furnished from scanning door 12, and compares it with the information received from reference source 24. The compared information is then displayed on a monitor 26.

Whether obtained with or without use of information from source 24, the interference between radiation 14b, which is reflected from the door, and reference beam 17 produces a characteristic pattern 28 known as "Newton's Rings" which take the form of nested bull's eye circles. This pattern provides a quantitative measure of the depth of each irregularity, which is determined by counting the contour lines around each circle so that the depth of a dent or other surface irregularity can be evaluated. If desired, the comparative information may also be displayed numerically. When the dent or other surface irregularity is within tolerance, no pattern 28 need be presented. When the dent or other surface irregularity is not within tolerance, pattern 28 not only appears, but its location on monitor 26 also identifies the location of the actual irregularity on door 12.

IR source 14, semi-transparent mirror 15, IR detector 18, charge-coupled device 20, comparator 22, reference source 24 and monitor 26 are all of conventional design. The wave length of the IR radiation from source 14 is selected in accordance with the minimum showing of unacceptable surface irregularities. For example, radiation of 10 micrometers or greater is sufficient to detect unacceptable dents in automobile body surfaces.

IR Source 14 preferably comprises a far infrared pulsed coherent source.

Comparator 22 optionally utilizes a conventional RMS (root mean square) error measurement computer program which, for each pixel in the area of interest, takes the difference between the reference standard signal and a test measurement signal, squares the differences, adds up the squares, divides the result by the total number of pixels, and takes the square root to obtain the average, that is, the RMS. This number serves as an overall "goodness-of-fit" measure which can be used to automatically trigger an alarm for samples that deviate too much from the standard.

Detector 18 comprises an array of half wave antennas, e.g., about 0.05 micrometers wide, made of metal on silicon. The junction between the quarter wave length halves is made to conduct in one direction only. Thus, one quarter wave length arm becomes positive, and the other negative. These actuate the gate of an F.E.T. structure built into the silicon beneath them. The outputs of the F.E.T.s inject electrons and holes into elements or "buckets" of a charge-coupled device adjacent to the F.E.T.s. After a charge is accumulated for a time, the array of charges is pumped out in the usual fashion to form a video signal which is forwarded to display monitor 26. This monitor will then show depths of a dent in 10 micrometer intervals.

Specifically, the holographic interference from the reflected radiation or waves produces pulses of current which become the intensity sources of a visual display through injection into charge-coupled device 20 and the standard video system embodied in monitor 26.

To avoid a requirement that sequential parts, such as automobile doors, be three-dimensionally aligned to within microns of reference points, means can be provided for movement of the IR detector array. Specifically, a displacement control 30 of conventional construction is coupled to IR detector array 18 and CCD 20, and is arranged to vibrate or otherwise physically displace the CCD and IR detector array, so that both can be two-dimensionally translated and rotated in a single plane which is roughly parallel to the line of sight to the door. During such movement, a number of sensed images of a given object are taken, one at each of the different positions of IR detector array 18. For each image, comparator 22 measures its correlation with a desired image stored in reference source 24. The image of highest correlation is then used to determine variations from the desired configuration. If greater accuracy is desired, displacement control 30 can also be arranged to translate along the line of sight.

For purposes of illustration, a given number of pixels per image, e.g., 100 by 100 pixels per image, is chosen. It is to be understood that a larger number may by used if more detail is desired. Then, a desired number of positions of the CCD assembly is further chosen for a given position, such as area 16 of door 12, with 100 positions being an acceptable number for the automobile door described herein. This totals 1,000,000 pixels which are to be stored in the short term memory of comparator 22. For a value of 10 bits per pixel, the total number of bits to be stored in the comparator memory accordingly is 10,000,000 bits.

Although the invention has been described with respect to a particular embodiment thereof, it should be realized that various changes and modifications may be made therein without departing from the spirit and scope of the invention.

We claim:

1. An infrared holographic defect detector comprising:
   means for providing infrared radiation and a reference signal therefrom and for directing the infrared radiation at a surface under test;
   means for receiving the reference signal and the radiation reflected from the surface to provide detected interference information; and
   means for determining the existence of any defect in the surface from the detected interference information, said determining means including means for providing desired interference information; and
   means for comparing the detected interference information to the desired interference information to determine the existence of a defect.

2. A detector according to claim 1 in which said providing means comprises a far infrared pulsed coherent source of infrared radiation.

3. A detector according to claim 1 in which said receiving means comprises a combined infrared detector and charge-coupled device.

4. A detector according to claim 1 further comprising means coupled to said determining means for visually displaying a quantitative measurement of the surface.

5. A detector according to claim 1 in which said determining means includes means for deriving a quantitative measurement of any such defect.

6. A detector according to claim 1 in which said comparing means is configured to utilize RMS error measurement.

7. A detector according to claim 1 further comprising a displacement control coupled to said receiving means for two-dimensionally translating and rotating said receiving means in a single plane which is roughly parallel to the line of sight to the surface under test, for obtaining a number of sensed images of the surface, one at each of the different positions of the receiving means and, thus, for enabling said determining means to measures its correlation with a desired image stored in a reference source and for obtaining the image of highest correlation to determine variations from the desired configuration.

8. An infrared holographic defect detector for detecting dents and other imperfections in a surface of an automobile body having a matt grey or like coating thereon, comprising:
   a far infrared pulsed coherent source of infrared radiation for providing infrared radiation of about 10 microns and a reference signal therefrom;
   means for directing the infrared radiation at a surface and any imperfections therein;
   means for receiving the reference signal and the radiation reflected from the surface comprising a combined infrared detector and charge-coupled device to provide detected interference information from the reflected radiation and the reference signal;

means for determining the existence of any imperfections in the surface from the detected interference information, and including means for providing desired interference information of a configuration of a desired surface and means for comparing the detected information with the desired interference information by utilizing RMS error measurement; and means for visually displaying the compared information in terms of a quantitative measurement and location of any such imperfections in the surface.

9. A method for scanning a surface of an article comprising the steps of:

providing desired interference information;

providing infrared radiation and a reference signal therefrom;

directing the infrared radiation at the surface;

receiving the radiation reflected from the surface; and determining the existence of any defect in the surface by comparing detected interference information, derived from interference between the reflected radiation and the reference signal, with the desired interference information.

10. A method according to claim 9 in which said information providing step comprises the steps of:

utilizing said steps of providing infrared radiation and a reference signal therefrom, directing the infrared radiation at the surface and receiving the radiation reflected from the surface, to determine the desired surface configuration information; and inputting the desired surface configuration information into a source for use in said comparing step.

11. A method according to claim 9 further comprising the steps of:

two-dimensionally translating and rotating the receiving means in a single plane which is roughly parallel to the line of sight to the surface;

obtaining a number of sensed images of the surface, one at each of several different positions of the receiving means; and correlating the sensed images with a desired image stored in a reference source for obtaining the image of highest correlation to determine variations from the desired configuration.

* * * * *